(12) United States Patent
McBride

(10) Patent No.: US 9,078,709 B2
(45) Date of Patent: Jul. 14, 2015

(54) SPINAL IMPLANT SYSTEM AND METHOD

(75) Inventor: Larry McBride, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 482 days.

(21) Appl. No.: 13/424,019

(22) Filed: Mar. 19, 2012

(65) Prior Publication Data

US 2013/0245702 A1 Sep. 19, 2013

(51) Int. Cl.
*A61B 17/70* (2006.01)
*A61B 17/56* (2006.01)
*A61B 17/86* (2006.01)

(52) U.S. Cl.
CPC ........... *A61B 17/7076* (2013.01); *A61B 17/708* (2013.01)

(58) Field of Classification Search
CPC .................. A61B 17/7076; A61B 17/708
USPC ................ 606/265–275, 104, 99, 86 A
See application file for complete search history.

(56) References Cited

U.S. PATENT DOCUMENTS

| | | | |
|---|---|---|---|
| 3,963,028 A | 6/1976 | Cooley et al. | |
| 5,336,170 A | 8/1994 | Salerno et al. | |
| 5,891,145 A | 4/1999 | Morrison et al. | |
| 7,226,413 B2 | 6/2007 | McKinley | |
| 7,476,240 B2 | 1/2009 | Raymond | |
| 7,491,218 B2 | 2/2009 | Landry et al. | |
| 7,563,264 B2 | 7/2009 | Landry et al. | |
| 7,575,581 B2* | 8/2009 | Lovell | 606/104 |
| 7,608,081 B2* | 10/2009 | Abdelgany | 606/103 |
| 7,666,189 B2 | 2/2010 | Gerber et al. | |
| 7,794,464 B2 | 9/2010 | Bridwell et al. | |
| 7,802,574 B2 | 9/2010 | Schultz | |
| 7,842,044 B2 | 11/2010 | Runco et al. | |
| 7,846,093 B2 | 12/2010 | Gorek et al. | |
| 7,854,751 B2* | 12/2010 | Sicvol et al. | 606/246 |
| 7,887,541 B2* | 2/2011 | Runco et al. | 606/86 A |
| 7,914,558 B2 | 3/2011 | Landry et al. | |
| 7,918,857 B2 | 4/2011 | Dziedzic et al. | |
| 7,918,858 B2 | 4/2011 | Stad et al. | |
| 7,922,746 B2 | 4/2011 | Miller | |
| 7,927,334 B2 | 4/2011 | Miller et al. | |
| 7,985,242 B2 | 7/2011 | Forton et al. | |
| 7,988,695 B2* | 8/2011 | Dye | 606/86 A |
| 8,012,141 B2 | 9/2011 | Wright et al. | |
| 8,096,996 B2 | 1/2012 | Gutierrez et al. | |
| 2005/0033299 A1* | 2/2005 | Shluzas | 606/61 |
| 2006/0074418 A1* | 4/2006 | Jackson | 606/61 |
| 2006/0079903 A1 | 4/2006 | Wong | |
| 2006/0111712 A1* | 5/2006 | Jackson | 606/61 |

(Continued)

*Primary Examiner* — Zade Coley
(74) *Attorney, Agent, or Firm* — Sorell Lenna & Schmidt LLP

(57) ABSTRACT

A spinal implant system includes a first member comprising walls that include a first end surface defining a first locking cavity, a second end surface and an outer surface extending therebetween. A second member includes a first arm having an inner surface that defines a first cavity and a second arm having an inner surface that defines a second cavity. The inner surface of the first arm includes a first projection disposable in the first cavity and the inner surface of the second arm includes a second projection disposable in the second cavity. A third member includes a first extension having an inner surface that defines a first cavity and a second extension having an inner surface that defines a second cavity. The third member is configured for axial translation relative to the second member between a first orientation and a second orientation. Methods of use are disclosed.

20 Claims, 12 Drawing Sheets

(56) References Cited

U.S. PATENT DOCUMENTS

| | | |
|---|---|---|
| 2006/0111715 A1 | 5/2006 | Jackson |
| 2006/0111730 A1 | 5/2006 | Hay |
| 2006/0122597 A1 | 6/2006 | Jones et al. |
| 2006/0247658 A1* | 11/2006 | Pond et al. .................. 606/104 |
| 2006/0264962 A1 | 11/2006 | Chin et al. |
| 2006/0293680 A1* | 12/2006 | Jackson ...................... 606/86 |
| 2007/0129731 A1* | 6/2007 | Sicvol et al. ................ 606/104 |
| 2007/0213714 A1 | 9/2007 | Justis |
| 2007/0233155 A1* | 10/2007 | Lovell ......................... 606/104 |
| 2007/0244493 A1 | 10/2007 | Bjerken |
| 2007/0270867 A1 | 11/2007 | Miller et al. |
| 2008/0015601 A1* | 1/2008 | Castro et al. ................ 606/86 |
| 2008/0172062 A1 | 7/2008 | Donahue et al. |
| 2008/0234678 A1 | 9/2008 | Gutierrez et al. |
| 2008/0243190 A1 | 10/2008 | Dziedzic et al. |
| 2009/0030419 A1* | 1/2009 | Runco et al. ................ 606/99 |
| 2009/0105771 A1 | 4/2009 | Lei et al. |
| 2009/0143828 A1 | 6/2009 | Stad et al. |
| 2009/0157125 A1 | 6/2009 | Hoffman et al. |
| 2009/0171391 A1 | 7/2009 | Hutton et al. |
| 2009/0222046 A1 | 9/2009 | Gorek |
| 2009/0228054 A1* | 9/2009 | Hoffman et al. ............ 606/86 A |
| 2009/0228055 A1* | 9/2009 | Jackson ...................... 606/86 A |
| 2009/0228056 A1 | 9/2009 | Jackson |
| 2009/0234395 A1* | 9/2009 | Hoffman et al. ............ 606/86 A |
| 2009/0264895 A1 | 10/2009 | Gasperut et al. |
| 2009/0318972 A1 | 12/2009 | Jackson |
| 2010/0030283 A1 | 2/2010 | King et al. |
| 2010/0036443 A1 | 2/2010 | Hutton et al. |
| 2010/0063552 A1 | 3/2010 | Chin et al. |
| 2010/0069972 A1 | 3/2010 | Jones et al. |
| 2010/0198268 A1 | 8/2010 | Zhang et al. |
| 2010/0198271 A1 | 8/2010 | Leone |
| 2010/0312279 A1 | 12/2010 | Gephart et al. |
| 2011/0015678 A1 | 1/2011 | Jackson |
| 2011/0022088 A1 | 1/2011 | Forton et al. |
| 2011/0106178 A1 | 5/2011 | Schwab |
| 2011/0202096 A1* | 8/2011 | White et al. ................. 606/86 R |
| 2011/0218581 A1 | 9/2011 | Justis |
| 2011/0264098 A1 | 10/2011 | Cobbs |
| 2011/0313463 A1* | 12/2011 | McLean ....................... 606/279 |
| 2011/0319938 A1* | 12/2011 | Piza Vallespir et al. ...... 606/264 |
| 2013/0103094 A1* | 4/2013 | Beale et al. .................. 606/279 |

* cited by examiner

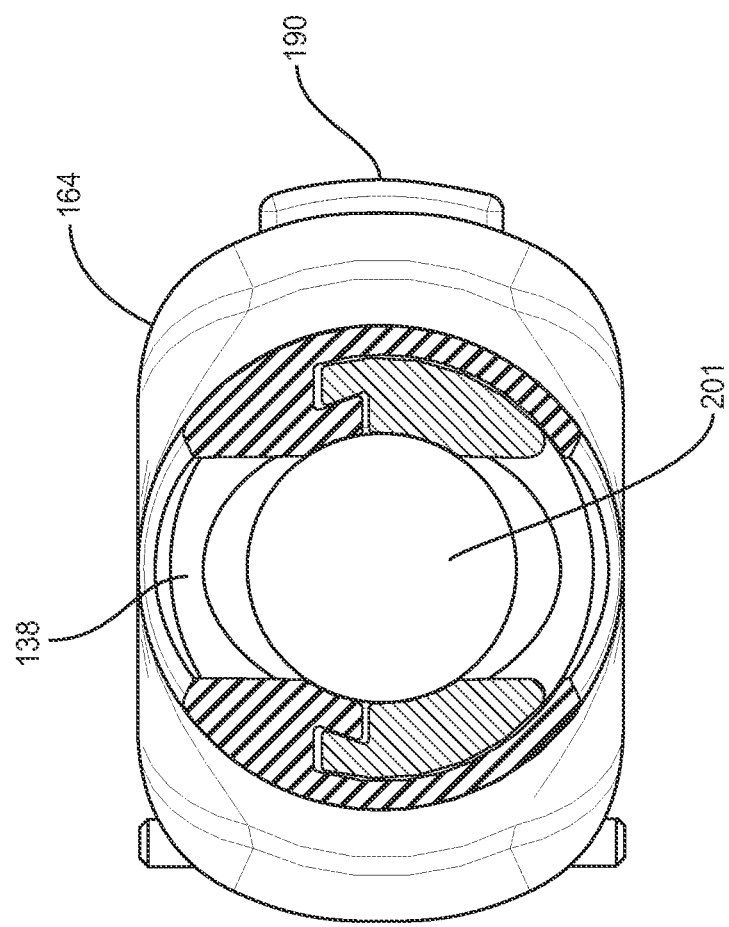

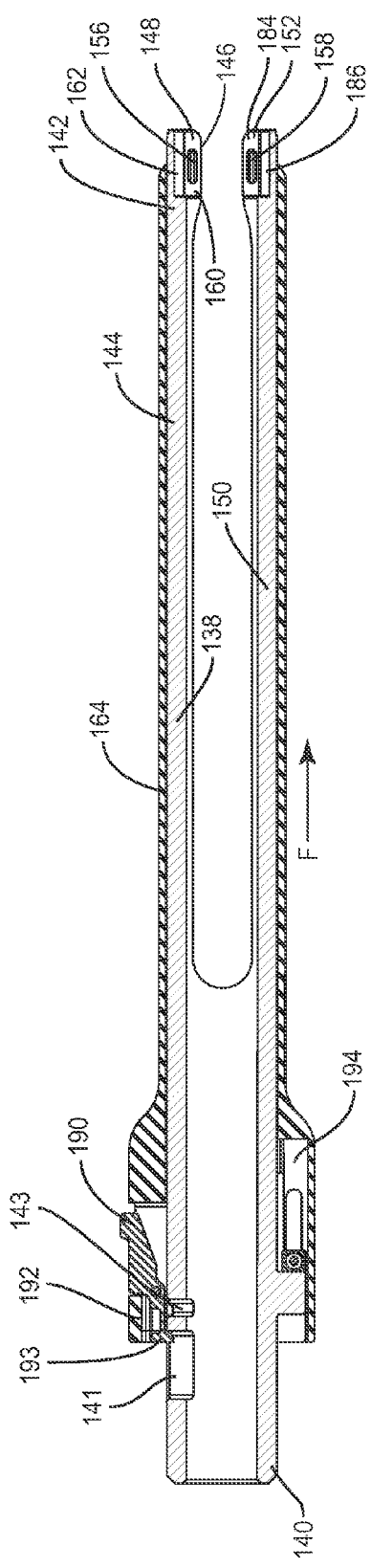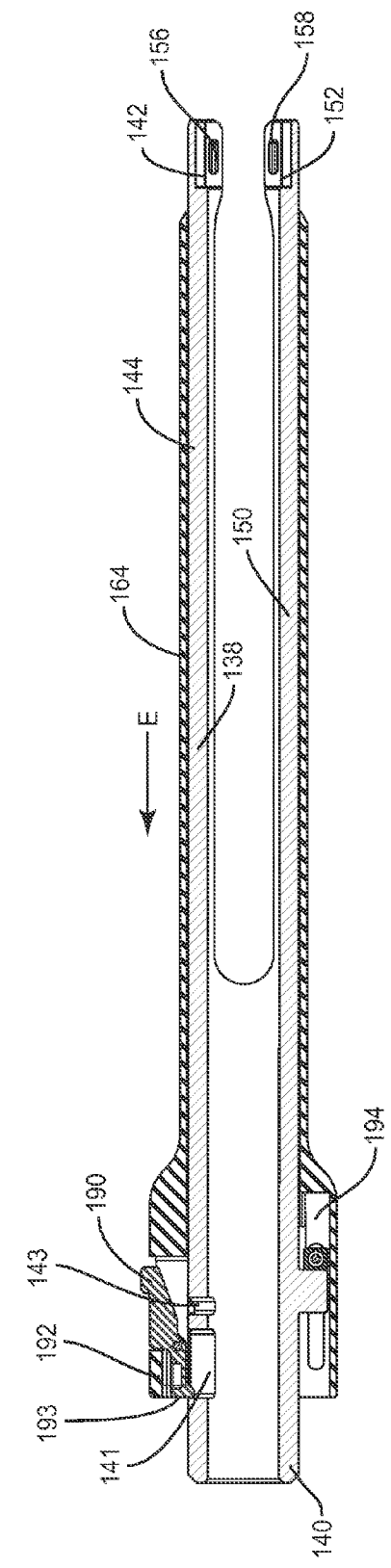

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, a spinal implant system is provided. The spinal implant system includes a first member comprising a proximal portion having a pair of spaced apart walls defining an implant cavity and a distal portion including a tissue penetrating portion. Each of the walls includes a first end surface defining a first locking cavity, a second end surface and an outer surface extending therebetween. A second member includes a first arm having an inner surface that defines a first cavity and a second arm having an inner surface that defines a second cavity. The inner surface of the first arm includes a first projection disposable in the first cavity and the inner surface of the second arm includes a second projection disposable in the second cavity. A third member includes a first extension and a second extension that define a longitudinal cavity configured for disposal of the second member. The first extension having an inner surface that defines a first cavity and the second extension having an inner surface that defines a second cavity. The third member is configured for axial translation relative to the second member between a first orientation such that the first and second projections of the second member extend distal to the third member to engage the first locking cavities and a second orientation such that the second end surfaces are disposed within the first and second cavities of the third member and the first end surfaces engage the inner surfaces of the first and second arms.

In one embodiment, the spinal implant system comprises a bone fastener that includes a receiver having a pair of spaced apart walls defining a U-shaped implant cavity and a shaft that includes a tissue penetrating portion. Each of the walls includes a first end surface that defines a first locking slot, a second end surface that defines a second locking slot and an outer surface that extends therebetween. The outer surface defines a third locking cavity. The bone fastener includes a first side portion and a second side portion. The first side portion includes the first end surfaces of each wall and the second side portion includes the second end surfaces of each wall. An extender extends between a proximal end and a distal end and includes a first cantilevered arm having an inner surface that defines a first capture cavity adjacent the distal end. The extender includes a second cantilevered arm having an inner surface that defines a second capture cavity adjacent the distal end. The inner surfaces include a first elongated projection that extends into the first cavity and a second elongated projection that extends into the second cavity. The inner surfaces that define the first and second cavities of the extender each include a planar face that engages with the first end surface and an arcuate face that engages with the outer surface of a respective wall such that the extender engages with the first side portion. A sleeve extends between a proximal end and a distal end and includes a first cantilevered extension and a second cantilevered extension that define a longitudinal cavity configured for slidable disposal of the extender. The first extension having an inner surface that defines a first capture cavity and the second extension having an inner surface that defines a second capture cavity. The inner surfaces define the first and second cavities of the sleeve and each include a planar face that engages with the second end surface and an arcuate face that engages with the outer surface of a respective wall such that the sleeve engages with the second side portion. A linkage actuator includes a first link connected to the proximal end of the extender at a first pivot point and a second link at a second pivot point. The second link being connected to the proximal end of the sleeve at a third pivot point. The first link including a handle that extends from the second pivot point and is rotatable relative to the extender. The handle is engaged such that the sleeve is caused to axially translate relative to the extender in a first direction for disposal in a first orientation such that the first and second projections extend distal to the sleeve to engage the first locking slots and to axially translate relative to the extender in a second direction for disposal in a second orientation such that the second end surfaces are disposed within the first and second cavities of the sleeve and the first end surfaces are engaged with the inner surfaces of the first and second arms with the projections disposed in the slots.

In one embodiment, the spinal implant system includes a bone fastener having a receiver including a pair of spaced apart walls defining a U-shaped implant cavity and a shaft that includes a tissue penetrating portion. Each of the walls includes a first end surface that defines a first locking slot. A second end surface defines a second locking slot and an outer surface extends therebetween and defines a third locking cavity. The bone fastener includes a first side portion and a second side portion. The first side portion includes the first end surfaces of each wall and the second side portion includes the second end surfaces of each wall. An extender extends between a proximal end and a distal end and includes a first cantilevered arm with an inner surface that defines a first capture cavity adjacent the distal end and a second cantilevered arm having an inner surface that defines a second capture cavity adjacent the distal end. The inner surfaces include a first elongated projection extendable into the first cavity and a second elongated projection extendable into the second cavity. The inner surface that defines the first and second cavities of the extender each include a planar face that engages with the first end surface and an arcuate face that engages with the outer surface of a respective wall such that the extender engages with the first side portion. The proximal end of the extender includes a first lateral opening and a second lateral opening. A sleeve extends between a proximal end and a distal end, and includes a first cantilevered extension and a second cantilevered extension that define a longitudinal cavity configured for slidable disposal of the extender. The first extension having an inner surface that defines a first capture cavity and the second extension having an inner surface that defines a second capture cavity. The inner surfaces define the first and second cavities of the sleeve and each include a planar face that engages with the second end surface and an arcuate face that engages with the outer surface of a respective wall such that the sleeve engages with the second side portion. An actuator includes a button mounted with the sleeve and a first biasing member disposed to bias the button into engagement with the extender. The actuator includes a second biasing member engaged with the extender to cause axial translation of the extender in a second direction. The button is disposable in the first lateral opening such that the sleeve is axially translatable relative to the extender in a first direction for disposal in a first orientation such that the first and second projections extend distal to the sleeve to engage the first locking slots and axially translate relative to the extender in the second direction for disposal in a second orientation such that the second end surfaces are disposed within the first and second cavities of the sleeve and the first end surfaces are engaging the inner surfaces of the first and second arms with the projections disposed in the slots. In the second orientation, the button is disposable in the second lateral opening such that the extender is locked relative to the sleeve.

BRIEF DESCRIPTION OF THE DRAWINGS

The present disclosure will become more readily apparent from the specific description accompanied by the following drawings, in which:

FIG. 11 is a bottom view of the components of the system shown in FIG. 10;

FIG. 12 is a side cross section view of the components of the system shown in FIG. 10;

FIG. 13 is a side cross section view of the components of the system shown in FIG. 10;

Like reference numerals indicate similar parts throughout the figures.

DETAILED DESCRIPTION

Figure 1:
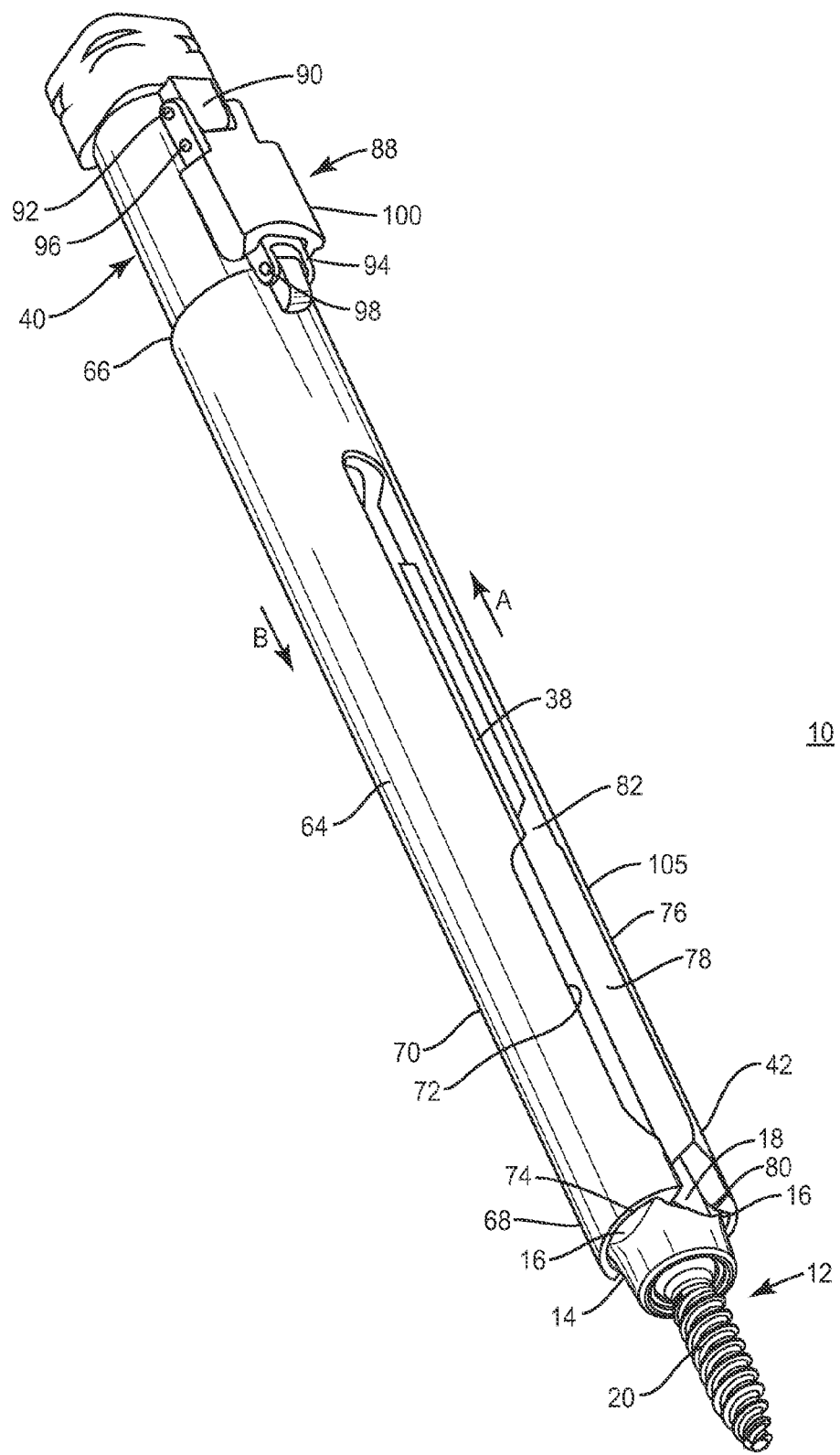
FIG. 1 is a perspective view of one particular embodiment of a system in accordance with the principles of the present disclosure.
Figure 2:
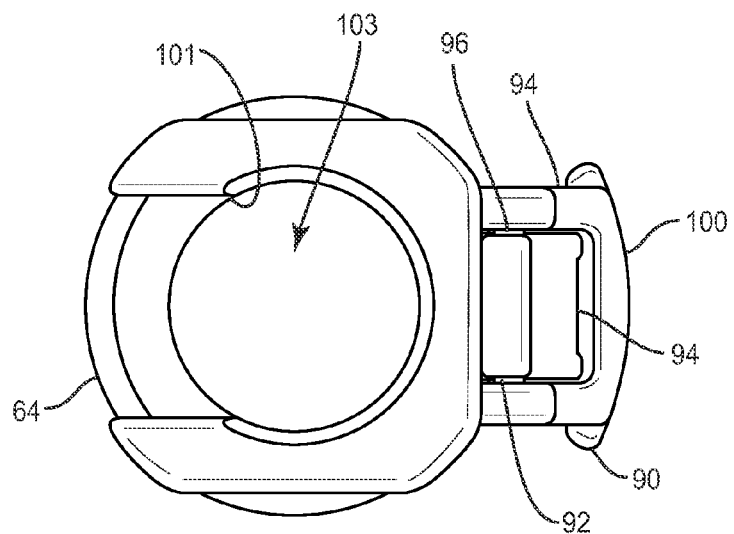
FIG. 2 is a top view of the system shown in FIG. 1.
Figure 3:
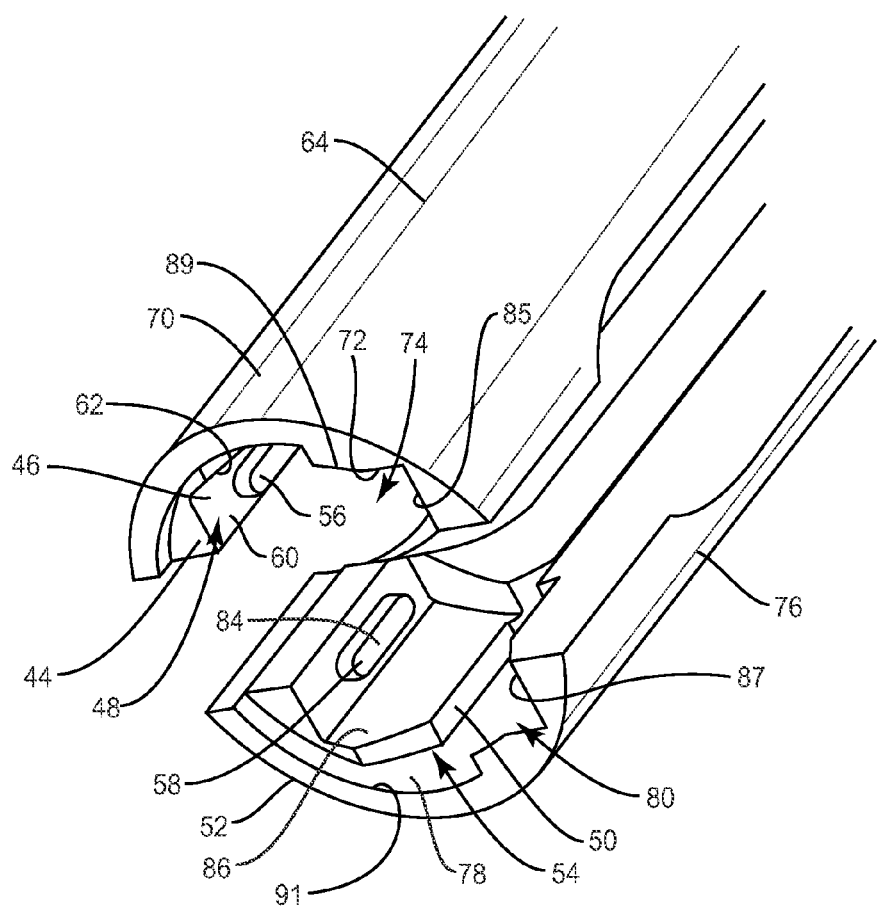
FIG. 3 is a break away perspective view of the system shown in FIG. 1.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. It is envisioned that the surgical implant system can include a bone fastener having a head with a cut that allows the head to be captured and retained under tension and lateral compression. It is further envisioned that the tension may be applied through a member, such as, for example, an extender and that compression may be applied through another member, such as, for example, a sleeve.

It is envisioned that the system may include instruments that are connected or attached to an extender(s) such as, for example, a lateral translation handle or derotation instruments. It is further envisioned that the system may have an extender with a quick release mechanism to allow the extender to slide into engagement with an implant. It is contemplated that the system can include an extender having features that prevent an implant from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-8, there is illustrated components of a surgical system, such as, for example, a spinal implant system 10 in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. It is contemplated that spinal implant system 10 and method may be employed with treatments using minimally invasive and percutaneous techniques.

Figure 8:
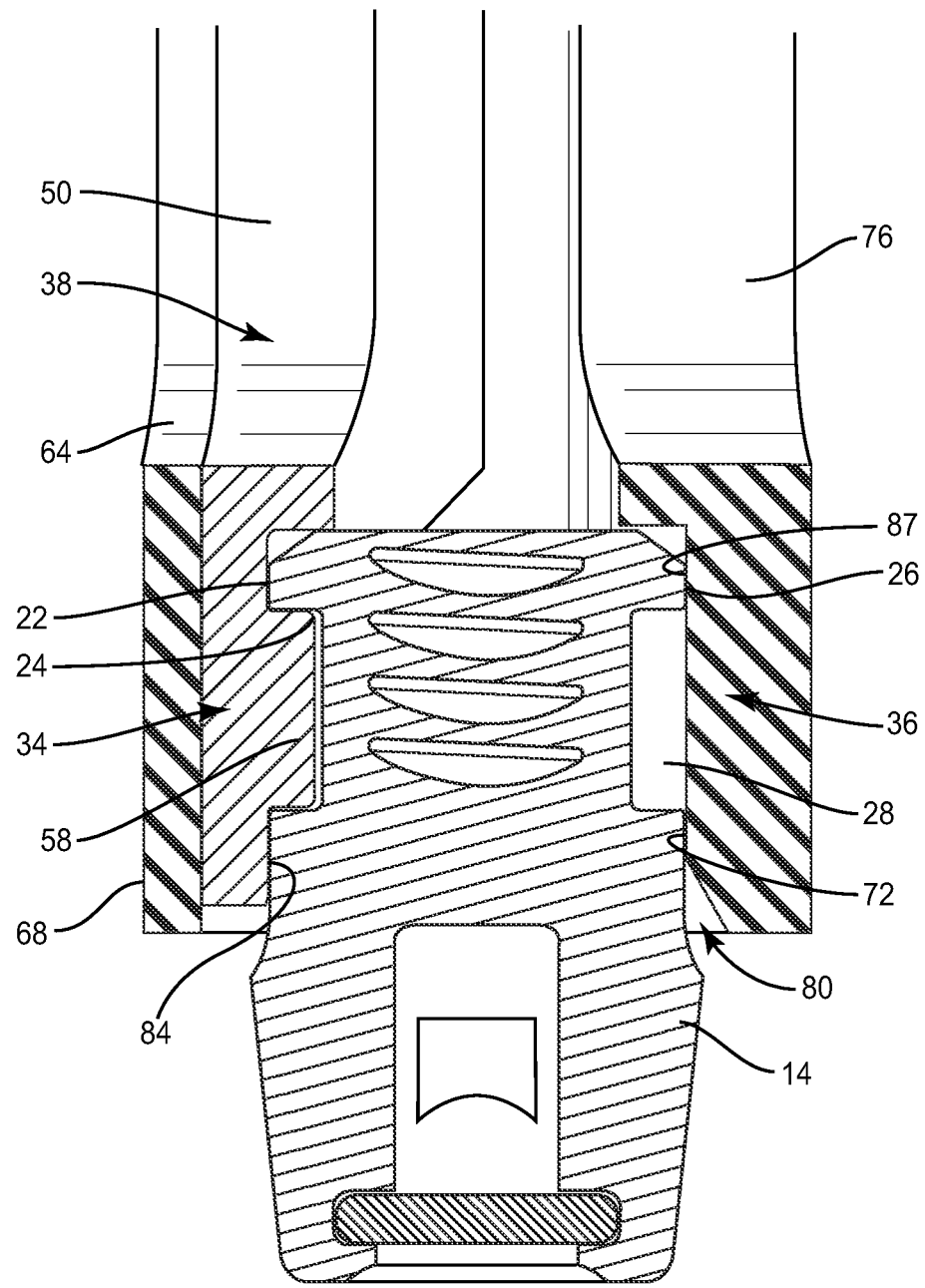
FIG. 8 is an enlarged cross section view of the system shown in FIG. 3.
Figure 17:
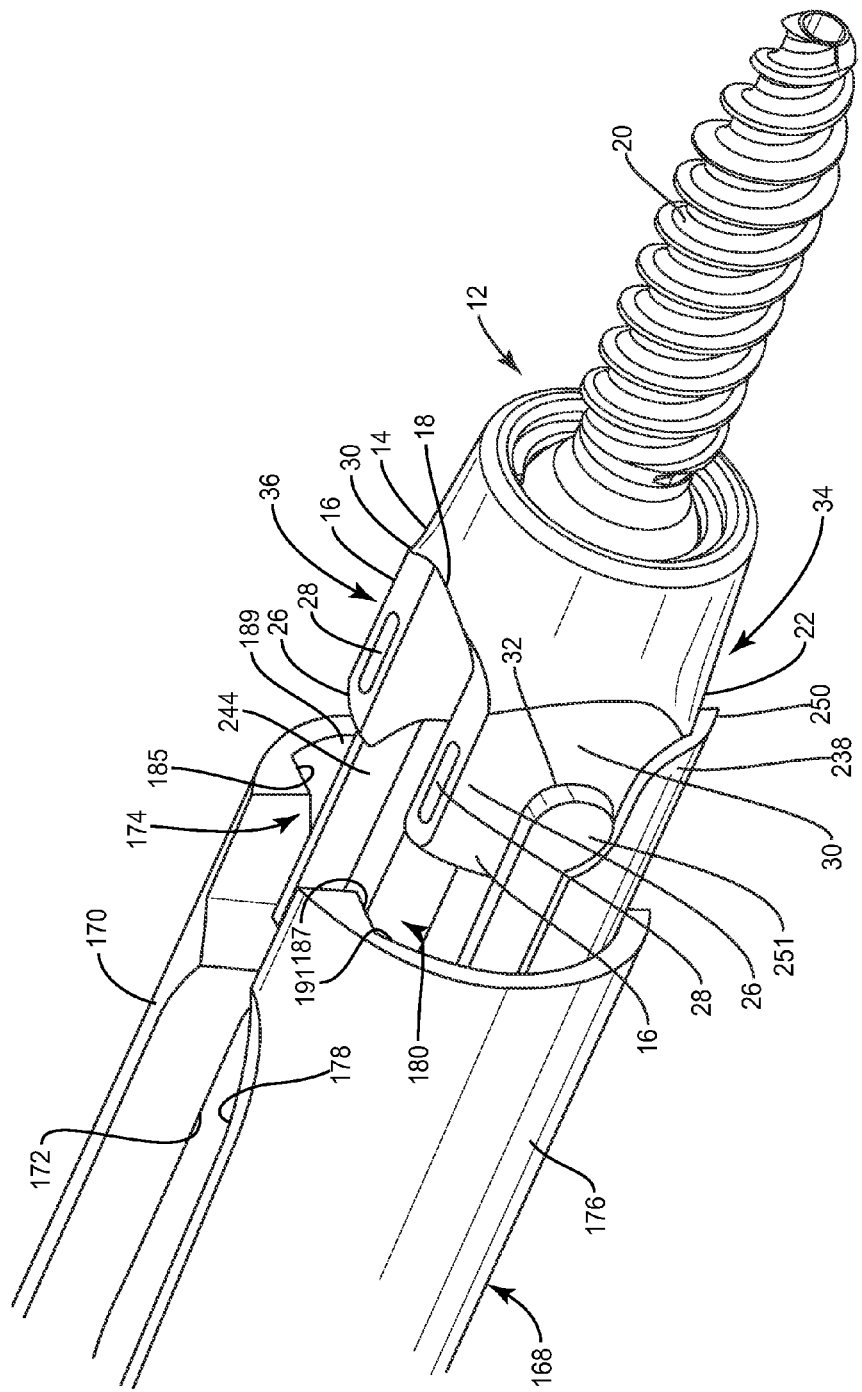
FIG. 17 is a break away perspective view of components of the system shown in FIG. 10.

Spinal implant system 10 includes a first member, such as, for example, a bone fastener 12. Bone fastener 12 includes a proximal portion, such as for example, a receiver 14 and a distal portion, such as for example, a shaft 20, as shown in FIGS. 8 and 17. Receiver 14 includes a pair of spaced apart walls 16 defining an implant cavity 18. It is envisioned that walls 16 may have uniformly increasing or decreasing taper, arcuate, staggered and/or offset portions. In one embodiment, the inner surfaces of walls 16 may include internal threads. Internal threads may be configured to receive a set screw to fix the position of a vertebral rod, for example, within implant cavity 18 of bone fastener 12. It is envisioned that internal threads may be reverse angle threads such that threads may include a forward face that points down and in toward implant cavity. In one embodiment, implant cavity 18 is generally U-shaped and is configured to receive a cylindrical spinal construct, such as, for example, a vertebral rod. It is contemplated that the cross-section of the vertebral rod may have various configurations, for example, round, oval, rectangular, polygonal, irregular, tapered, offset, staggered, uniform and non-uniform. It is envisioned that implant cavity 18 may have other configurations, including, for example, V-shaped, polygonal, or tapered depending upon the geometry of the spinal construct to be received within implant cavity 18.

Walls 16 include a first end surface 22 defining a first locking cavity, such as, for example an elongated locking slot 24 and a second end surface 26 defining a second locking cavity, such as, for example an elongated locking slot 28. Locking slots 24 and 28 have an oval cross section. It is envisioned that locking slots 24 and 28 may have other cross-sectional configurations, including, for example, flat bottomed channel, a cut similar to a rack and pinion, V-shaped, W-shaped, polygonal or tapered. It is further envisioned that one or both of slots 24 and 28 may be transversely oriented relative to a longitudinal axis of bone fastener 12, such as, for example, perpendicular, angled, and/or may be disposed in parallel orientation. It is contemplated that slots 24 and 28 allow bone fastener 12 to be captured and retained under tension and lateral compression by an extender 38, discussed below. It is envisioned that one or all of the surfaces of walls 16 have alternate surface configurations, such as, for example, rough, threaded for connection with surgical instruments, arcuate, undulating, porous, semi-porous, dimpled, polished and/or textured according to the requirements of a particular application.

An outer surface 30 extends between the first end surface 22 and the second end surface 26. Outer surface 30 defines a third locking cavity 32. Locking cavity 32 is oval in shape. It is contemplated that locking cavity 32 may have alternate cross-sectional configurations, including, for example, flat bottomed channel, a cut similar to a rack and pinion, V-shaped, W-shaped, polygonal or tapered. Bone fastener 12 includes a first side portion 34 and a second side portion 36. The first side portion 34 includes first end surfaces 22 of each wall and second side portion 36 includes second end surfaces 26 of each wall.

It is contemplated that shaft 20 or portions thereof can have various dimensions, for example, with regard to length, width, diameter, and thickness. Shaft 20 is threaded along the length thereof and configured for penetrating tissue. Shaft 20 has a cylindrical cross section configuration and includes an outer surface having an external thread form. It is contemplated that the thread form may include a single thread turn or a plurality of discrete threads. It is further contemplated that other engaging structures may be located on shaft 20, such as, for example, a nail configuration, barbs, expanding elements, raised elements and/or spikes to facilitate engagement of shaft 20 with tissue, such as, for example, vertebrae.

It is envisioned that all or only a portion of shaft 20 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 20 may include one or a plurality of openings. It is further contemplated that all or only a portion of the outer surface of shaft 20 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 20 may be disposed at various orientations, relative to the longitudinal axis of bone fastener 12, such as, for example, transverse, perpendicular and/or other angular orientations such as acute or obtuse and/or may be offset or staggered. It is further envisioned that all or only a portion of shaft 20 may be cannulated.

A second member, such as, for example, an extender 38 is provided for engaging bone fastener 12. Extender 38 extends between a proximal end 40 and a distal end 42. Extender 38 includes a first arm, such as for example, a first cantilevered arm 44 and a second arm, such as, for example, a second cantilevered arm 50. First cantilevered arm 44 includes an inner surface 46 that defines a first capture cavity 48 disposed adjacent the distal end 42. Second cantilevered arm 50 includes an inner surface 52 that defines a second capture cavity 54 disposed adjacent the distal end 42.

Inner surface 46 includes a first elongated projection 56 that extends into first cavity 48. Inner surface 52 includes a second elongated projection 58 that extends into the second cavity 54. Inner surface 46 includes a planar face 60 and inner surface 52 includes a planar face 84 that engages first end surfaces 22. Inner surface 46 includes an arcuate face 62 engageable with outer surface 30 of a respective wall 16 and inner surface 52 includes an arcuate face 86 engageable with the outer surface 30 of a respective wall 16 such that the extender 38 is engageable with the first side portion 34.

First and second locking slots 24, 28 are configured to receive first and second elongated projections 56, 58 of extender 38. It is contemplated that the depth of first and second locking slots 24, 28 corresponds to the depth of first and second elongated projections 56, 58 of extender 38. It is envisioned that one or both of first and second locking slots 24, 28 may be oriented parallel relative to a longitudinal axis of bone fastener 12 or other orientations, such as, for example, perpendicular, angled, and/or may be disposed in transverse orientation relative to a longitudinal axis of bone fastener 12. In one embodiment, walls 16 and/or outer surface 30 can include multiple locking slots, such as, for example, multiple recesses or multiple transverse grooves.

A third member, such as, for example, a sleeve 64 is configured for disposal of extender 38. Sleeve 64 extends between a proximal end 66 and a distal end 68. Sleeve 64 includes a first extension, such as, for example, a first cantilevered extension 70 and a second extension, such as, for example, a second cantilevered extension 76. Extensions 70 and 76 define a longitudinal cavity 82 configured for slidable disposal of extender 38.

First extension 70 includes an inner surface 72 that defines a first capture cavity 74. Second extension 76 includes an inner surface 78 that defines a second capture cavity 80. Inner surface 72 defines a planar face 85 engageable with second end surfaces 26 and inner surface 78 defines a planar face 87 engageable with second end surfaces Inner surface 72 defines an arcuate face 89 engageable with the outer surface 30 of a respective wall 16 and inner surface 78 defines an arcuate face 91 engageable with the outer surface 30 of a respective wall 16 such that sleeve 64 is engageable with the second side portion 36. It is further envisioned that one or all of the surfaces of sleeve 64 may have alternate surface configurations, such as, for example, rough, threaded for connection with surgical instruments, arcuate, undulating, porous, semi-porous, dimpled, polished and/or textured according to the requirements of a particular application. Inner surfaces 72, 78 are configured to engage second side portion 36 to facilitate capture and retention of bone fastener 12 and prevent bone fastener 12 from disengaging from extender 38 and sleeve 70 and/or rotating relative to extender 38 and sleeve 70.

An actuator is disposed between and/or connected with sleeve 64 and/or extender 38. The actuator is engaged to dispose extender 38 between a first orientation and a second orientation. In one embodiment, as shown in FIGS. 4-7, the actuator is a linkage actuator 88. Linkage actuator 88 includes a first link 90 connected to the proximal end 40 of the extender 38 at a first pivot point 92. A second link 94 is connected to first link 90 at a second pivot point 96. Second link 94 is connected to the proximal end 66 of the sleeve 64 at a third pivot point 98. First link 90 includes a handle 100 extending from the second pivot point 96 and is rotatable relative to the extender 38 to drive sleeve 64 in an axial direction relative to extender 38.

Figure 4:
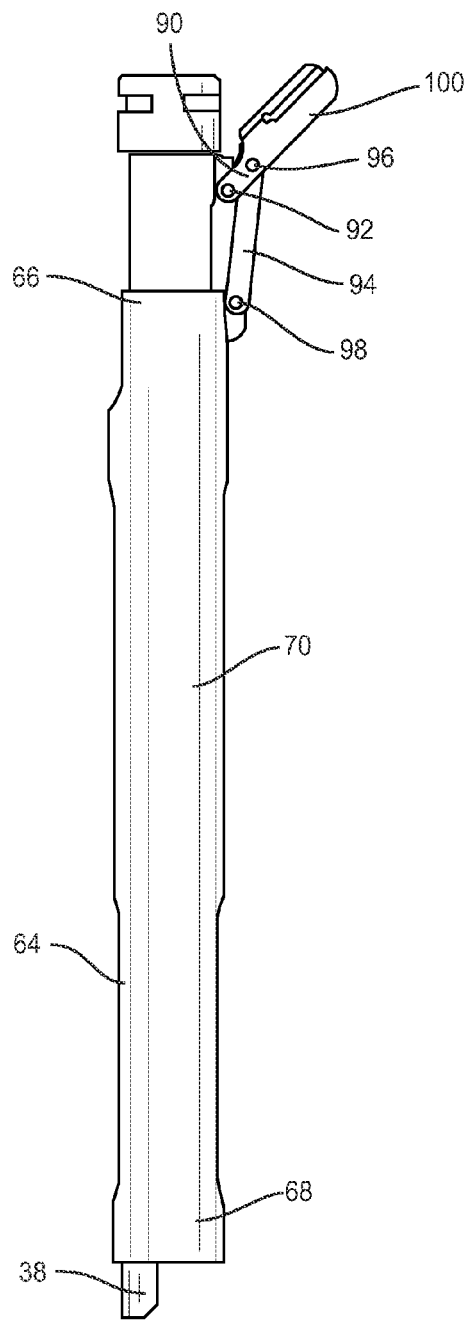
FIG. 4 is a side view of the system shown in FIG. 1.
Figure 5:
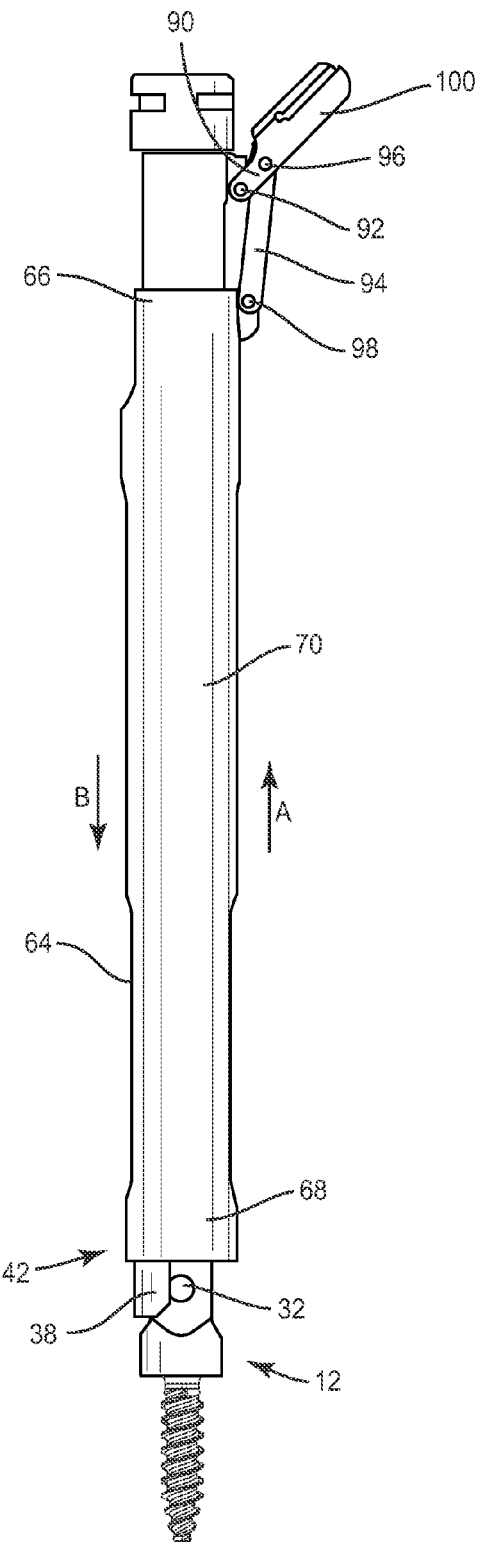
FIG. 5 is a side view of the system shown in FIG. 1.
Figure 6:
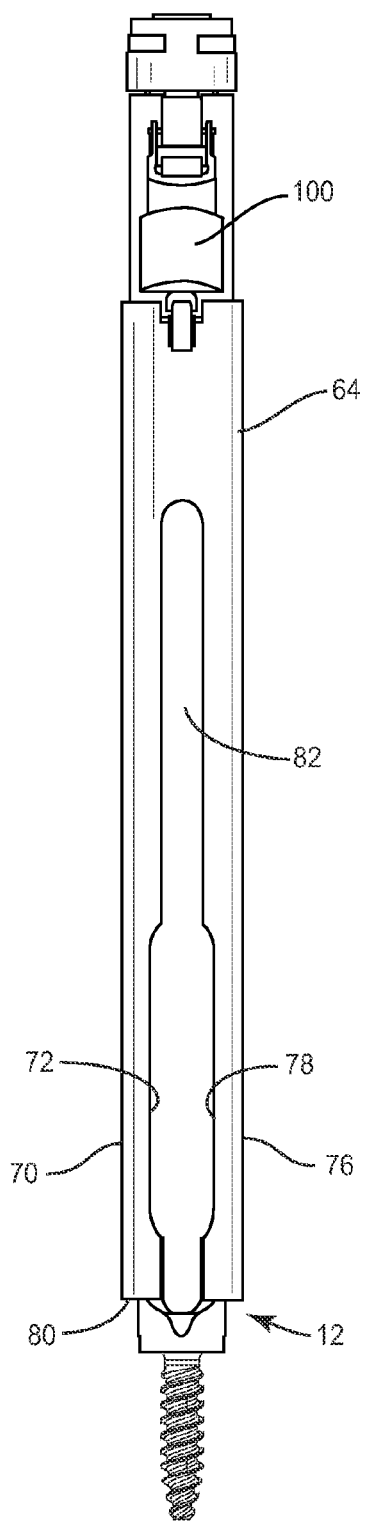
FIG. 6 is a side view of the system shown in FIG. 1.
Figure 7:
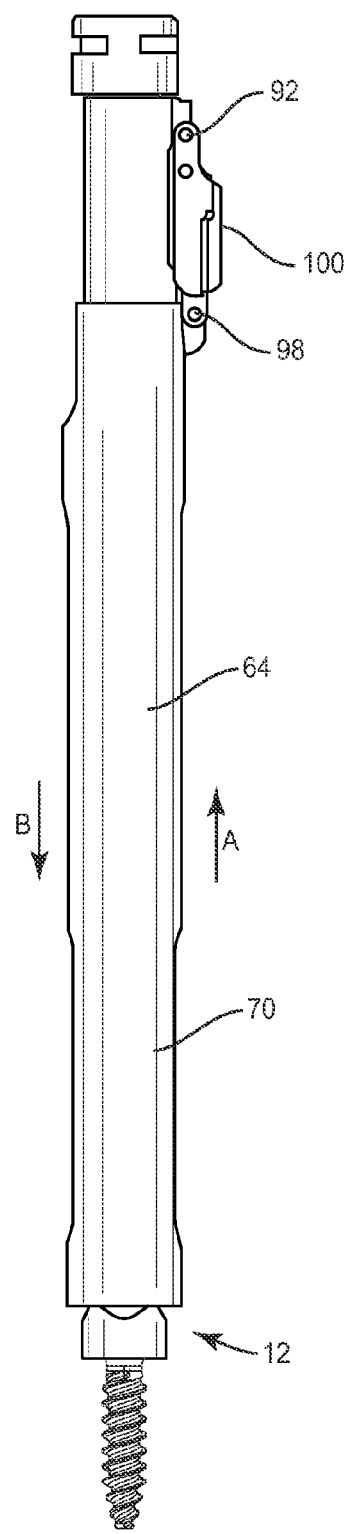
FIG. 7 is a side view of the system shown in FIG. 1.

Handle 100 is employed to move actuator 88 for rotation of its links to drive sleeve 64 in an axial direction between a first orientation, as shown in FIGS. 4 and 5, and a second orientation, as shown in FIGS. 6 and 7. Handle 100 is engaged with sleeve 64 such that sleeve 64 axially translatable relative to the extender 38 in a first direction, as shown by arrow A, and a second direction, as shown by arrow B. In the first orientation, first and second arms 44, 50 including projections 56, 58 extend distal to sleeve 64 to engage the first locking slots 24. Handle 100 is manipulated for rotation in a clockwise direction such that sleeve 64 axially translates in the direction shown by arrow B for disposal in the second orientation such that the second end surfaces 26 are disposed within the first and second cavities 74, 80 of sleeve 64 and the first end surfaces 22 are engaged with the inner surfaces 72, 78 of the first and second extensions 70, 76 with projections 56, 58 disposed within and fixed with slots 24.

In operation, to provisionally capture bone fastener 12, a medical practitioner rotates handle 100 in a counter clockwise direction to axially move sleeve 64 in the first direction as shown by arrow A to the first orientation of extender 38 and sleeve 64. In the first orientation, distal end 42 of extender 38 extends from distal end 68 of sleeve 64 to engage bone fastener 12. Projections 56, 58 engage slots 24 for fixation of extender 38 with bone fastener 12.

To move extender 38 and sleeve 64 to the second orientation, handle 100 is rotated about pivot 92 in a clockwise direction to axially move sleeve 64 in the second direction as shown by arrow B. First link 90 rotates relative to pivot 92 to drive second link 94 axially. As sleeve 64 moves in the second direction, extender 38 is drawn proximally within sleeve 64 causing distal ends 42 of first and second arms 44, 50, including first and second elongated projections 56, 58 to recess within distal end 68 of sleeve 64. Extender 38 engages bone fastener 12 such that first and second elongated projections 56, 58 of extender 38 are disposed within and fixed with locking slots 24. Arms 44, 50 engage first side portion 34 such that planar faces 60, 84 engage first end surfaces 22 and arcuate faces 62, 86 engage outer surfaces 30.

In the second orientation, distal end 42 of extender 38 is disposed within sleeve 64. Inner surfaces 72, 78 are facing and/or engaging in a close fitting contact with bone fastener 12 such that second end surfaces 26 are disposed in first and second cavities 74, 80 of sleeve 64. Extensions 70, 76 engage second side portion 36 such that planar faces 85, 87 engage second end surfaces 26 and arcuate faces 89, 91 engage outer surfaces 30. This configuration secures bone fastener 12 with extender 38/sleeve 64 and prevents ejection of bone fastener 12 from extender 38/sleeve 64 and/or rotation of receiver 14.

Upon fixation of bone fastener 12 and/or other components of spinal implant system 10, sleeve 64 and extender 38 are disposable in the first orientation to eject bone fastener 12 or extender 38. To eject and/or release bone fastener 12 from extender 38/sleeve 64, the medical practitioner rotates handle 100 in a counter clockwise direction to axially move sleeve 64 in the first direction as shown by arrow A to the first orientation of extender 38 and sleeve 64. Distal end 42 of extender 38 extends from distal end 68 of sleeve 64. The components of extender 38/sleeve 64 are manipulated to release bone fastener 12 from engagement such that projections 56, 58 are disengaged from slots 24 and bone fastener 12 is fixed securely with tissue according to the particular application.

Figure 9:
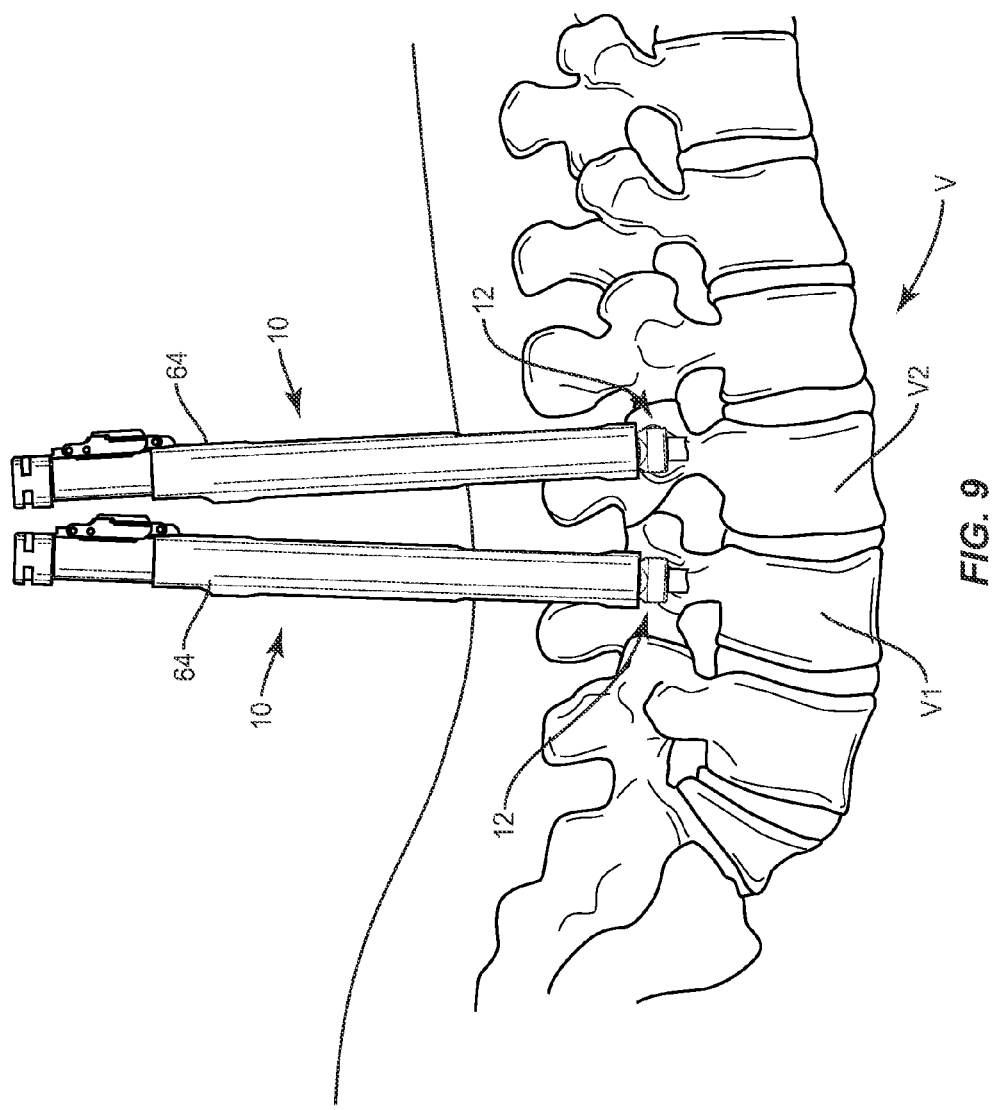
FIG. 9 is a side view of one embodiment of a system comprising the components shown in FIG. 1 disposed with vertebrae.

In assembly, operation and use, the spinal implant system 10 is employed with a surgical procedure for treatment of a spinal disorder affecting a section of a spine of a patient, as discussed herein. Spinal implant system 10 may also be employed with other surgical procedures. For example, spinal implant system 10 can be used with a surgical procedure for treatment of a condition or injury of an affected section of the spine including vertebrae V, as shown in FIG. 9.

In use, to treat the affected section of vertebrae V, a medical practitioner obtains access to a surgical site including vertebrae V1, V2 in any appropriate manner, such as through incision and retraction of tissues. It is envisioned that the spinal implant system 10 may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. The spinal implant system is then employed to augment the surgical treatment. The spinal implant system can be delivered or implanted as a pre-assembled device or can be assembled in situ. The spinal implant system may be completely or partially revised, removed or replaced, for example, removing bone fastener 12, sleeve 64 and/or extender 38, a vertebral rod and/or one or all of the components of the spinal implant system during or after the surgical procedure.

Pilot holes or the like are made in vertebrae V1, V2 for receiving shaft 20 of bone fastener 12. The spinal implant system 10 is disposed adjacent vertebrae V at a surgical site and the components of spinal implant system 10 are manipulable to drive, torque, insert or otherwise connect bone fastener 12 to vertebrae and/or dispose a vertebral construct, such as, for example, a vertebral rod (not shown) with bone fastener 12, according to the particular requirements of the surgical treatment.

Handle 100 is rotated in a counter clockwise direction, as discussed above, to axially translate sleeve 64 in the first direction, as shown by arrow A in FIG. 5, to provisionally capture bone fastener 12 in the first orientation of extender 38 and sleeve 64. Distal end 42 extends from distal end 68 to engage bone fastener 12. Projections 56, 58 engage slots 24 for fixation of extender 38 with bone fastener 12.

Bone fastener 12 is secured with extender 38 and sleeve 64 to facilitate the surgical treatment, by moving extender 38 and sleeve 64 to the second orientation. Handle 100 is rotated in a clockwise direction, as discussed above, to axially translate sleeve 64 in the second direction as shown by arrow B. Extender 38 is drawn proximally within sleeve 64 causing distal ends 42 of first and second arms 44, 50, including first and second elongated projections 56, 58 to recess within distal end 68. Extender 38 engages bone fastener 12 such that first and second elongated projections 56, 58 of extender 38 are disposed within and fixed with locking slots 24. Arms 44, 50 engage first side portion 34 such that planar faces 60, 84 engage first end surfaces 22 and arcuate faces 62, 86 engage outer surfaces 30.

In the second orientation, distal end 42 of extender 38 is disposed within sleeve 64. Inner surfaces 72, 78 are facing and/or engaging in a close fitting contact with bone fastener 12 such that second end surfaces 26 are disposed in first and second cavities 74, 80 of sleeve 64. Extensions 70, 76 engage second side portion 36 such that planar faces 85, 87 engage second end surfaces 26 and arcuate faces 89, 91 engage outer surfaces 30. This configuration secures bone fastener 12 with extender 38/sleeve 64 and prevents ejection of bone fastener 12 from extender 38/sleeve 64 and/or rotation of receiver 14.

Proximal end 40 and/or the actuator include an inner surface 101, which defines a passageway 103. Passageway 103 is configured for disposal and passage of instruments (not shown), such as, for example, a driver for applying torque and driving bone fastener 12 into vertebrae V1, V2 and/or a rod reducer, which may be passed through passageway 103 while sleeve 64 and extender 38 are disposed in the second orientation. Extensions 70 and 76 define lateral opening 105 that communicates with longitudinal cavity 82. In one embodiment, opening 105 and/or passageway 103 are configured for disposal and/or employed for delivery of implants, such as, for example, bone fastener 12 and/or a spinal construct, such as, for example, a spinal rod of spinal implant system 10.

Upon fixation of bone fastener 12 and/or other components of spinal implant system 10, sleeve 64 and extender 38 are disposable in the first orientation to eject bone fastener 12 or extender 38. To eject and/or release bone fastener 12 from extender 38/sleeve 64, handle 100 is rotated in a counter clockwise direction to axially translate sleeve 64 in the first direction to the first orientation. Distal end 42 extends from distal end 68. The components of extender 38/sleeve 64 are manipulated to release bone fastener 12 from engagement such that projections 56, 58 are disengaged from slots 24 and bone fastener 12 is fixed securely with V1, V2. Upon completion of the procedure, the surgical instruments and assemblies are removed from the surgical site and the incision is closed.

Bone fastener 12 may be employed as a bone screw, pedicle screw, or multi-axial screw used in spinal surgery. It is contemplated that bone fastener 12 may be coated with an osteoconductive material such as hydroxyapatite and/or osteoinductive agent such as a bone morphogenic protein for enhanced bony fixation. Bone fastener 12 can be made of radiolucent materials such as polymers. Radiomarkers may be included for identification under x-ray, fluoroscopy, CT, or other imaging techniques. Metallic or ceramic radiomarkers, such as tantalum beads, tantalum pins, titanium pins, titanium endcaps, and platinum wires can be used.

In one embodiment, as shown in FIGS. 10-17, spinal implant system 10, similar to the configurations and methods described above with regard to FIGS. 1-9, includes bone fastener 12, described above, which is configured to be captured and retained under tension and lateral compression by a second member, such as, for example, an extender 138.

Extender 138 extends between a proximal end 140 and a distal end 142. Extender 138 includes a first arm, such as for example, a first cantilevered arm 144 and a second arm, such a, for example, a second cantilevered arm 150. First cantilevered arm 144 includes an inner surface 146 that defines a first capture cavity 148 adjacent the distal end 142. Second cantilevered arm 150 includes an inner surface 152 that defines a second capture cavity 154 adjacent the distal end 142.

Inner surface 146 includes a first elongated projection 156 that extends into first cavity 148. Inner surface 152 includes a second elongated projection 158 that extends into the second cavity 154. Inner surface 146 includes a planar face 160 and inner surface 152 includes a planar face 184 that engages first end surfaces 22. Inner surface 146 includes an arcuate face 162 engageable with outer surface 30 of a respective wall 16 and inner surface 152 includes an arcuate face 186 engageable with the outer surface 30 of a respective wall 16 such that the extender 138 is engageable with the first side portion 34.

First locking slots 24 are configured to receive first and second elongated projections 156, 158 on the distal end of extender 138. Extender 138 includes a first lateral opening 141 disposed at the proximal end 140 and a second lateral opening 143 disposed at the proximal end 140. Lateral openings 141, 143 are utilized with actuator 188, discussed below.

A third member, such as, for example, a sleeve 164 extends between a proximal end 166 and a distal end 168. Sleeve 164 includes a first cantilevered extension 170 and a second cantilevered extension 176. Extensions 170 and 176 define a longitudinal cavity configured for slidable disposal of extender 138.

First extension 170 includes an inner surface 172 that defines a first capture cavity 174, as shown in FIG. 17. Second extension 176 includes an inner surface 178 that defines a second capture cavity 180. Inner surface 172 defines a planar face 185 engageable with second end surfaces 26 and inner surface 178 defines a planar face 187 engageable with second end surfaces 26. Inner surface 172 defines an arcuate face 189 engageable with the outer surface 30 of a respective wall 16 and inner surface 178 defines an arcuate face 191 engageable with the outer surface 30 of a respective wall 16 such that sleeve 164 is engageable with the second side portion 36.

Actuator 188 includes a depressible member, such as, for example, a button 190 including a tab 193. Button 190 is mounted with sleeve 164 and rotatable relative to sleeve 164 about a pivot point to engage extender 138. Button 190 includes a recess disposed adjacent tab 193, which is configured for disposal of a first biasing member, such as, for example a compression spring 192. Spring 192 is disposed between and engages sleeve 164 and button 190 to bias tab 193 into lateral openings 141, 143 of extender 138 to fix and/or lock extender 138 with sleeve 164 in an orientation, as described below. Tab 193 is disposable in lateral opening 143 to position extender 138 and sleeve 164 in a locked position (FIG. 16) in the second orientation, described above. Tab 193 is disposable in lateral opening 141, which is a load window. Lateral opening 141 provides a range of movement of tab 193 in the load window for movement of extender 138 relative to sleeve 164 between the second orientation and the first orientation, described above. Tab 193 is disposable in a distal-most position of lateral opening 141 to position extender 138 and sleeve 164 in a loaded and/or provisional capture position (FIG. 12) in the second orientation. Tab 193 is disposable in a proximal-most position of lateral opening 141 to position extender 138 and sleeve 164 in an eject or loading position (FIG. 13) in the first orientation.

Sleeve 164 includes a cavity 195, which is configured for disposal of a second biasing member such as, for example, a compression spring 194. Spring 194 engages a stop 196 connected with extender 138 and is engageable with sleeve 164 to facilitate axial translation of sleeve 164 relative to extender 138 in a first direction, as shown by arrow E in FIGS. 13 and 16, and a second direction, as shown by arrow F in FIGS. 12 and 16.

In operation, to provisionally capture bone fastener 12, a medical practitioner engages button 190 such that button 190 rotates and tab 193 pivots out of opening 143. Extender 138 is free to axially translate under the bias of spring 194. Extender 138 is manipulated against the bias of spring 194 and advanced in the first direction as shown by arrow F, as shown in FIG. 12. Button 190 pivots under the bias of spring 192 such that tab 193 enters and is disposed in opening 141. Extender 138 is free to axially translate within the range of movement provided by the load window of opening 141.

Sleeve 164 is held or otherwise fixed relative to extender 138 and extender 138 is manipulated against the bias of spring 194 and further advanced in the first direction as shown by arrow F to the first orientation. Tab 193 is disposed in the proximal-most position of opening 141 to position extender 138 and sleeve 164 in a loading position, as shown in FIG. 13. In the first orientation, distal end 142 of extender 138 extends from distal end 168 of sleeve 164 to engage bone fastener 12. Projections 156, 158 engage slots 124 for fixation of extender 138 with bone fastener 12.

Upon loading bone fastener 12 with extender 138, extender 138 is released such that spring 194 biases extender 138 in the second direction as shown by arrow E to the loaded and/or provisional capture position (FIG. 12) in the second orientation. As sleeve 164 moves in the second direction, extender 138 is drawn proximally within sleeve 164 causing distal ends 142 of first and second arms 144, 150, including first and second elongated projections 156, 158, to recess within distal end 168. Extender 138 engages bone fastener 12 such that first and second elongated projections 156, 158 of extender 138 are disposed within and fixed with locking slots 24. Arms 144, 150 engage first side portion 34 such that planar faces 160, 184 engage first end surfaces 22 and arcuate faces 162, 186 engage outer surfaces 30.

Figure 10:
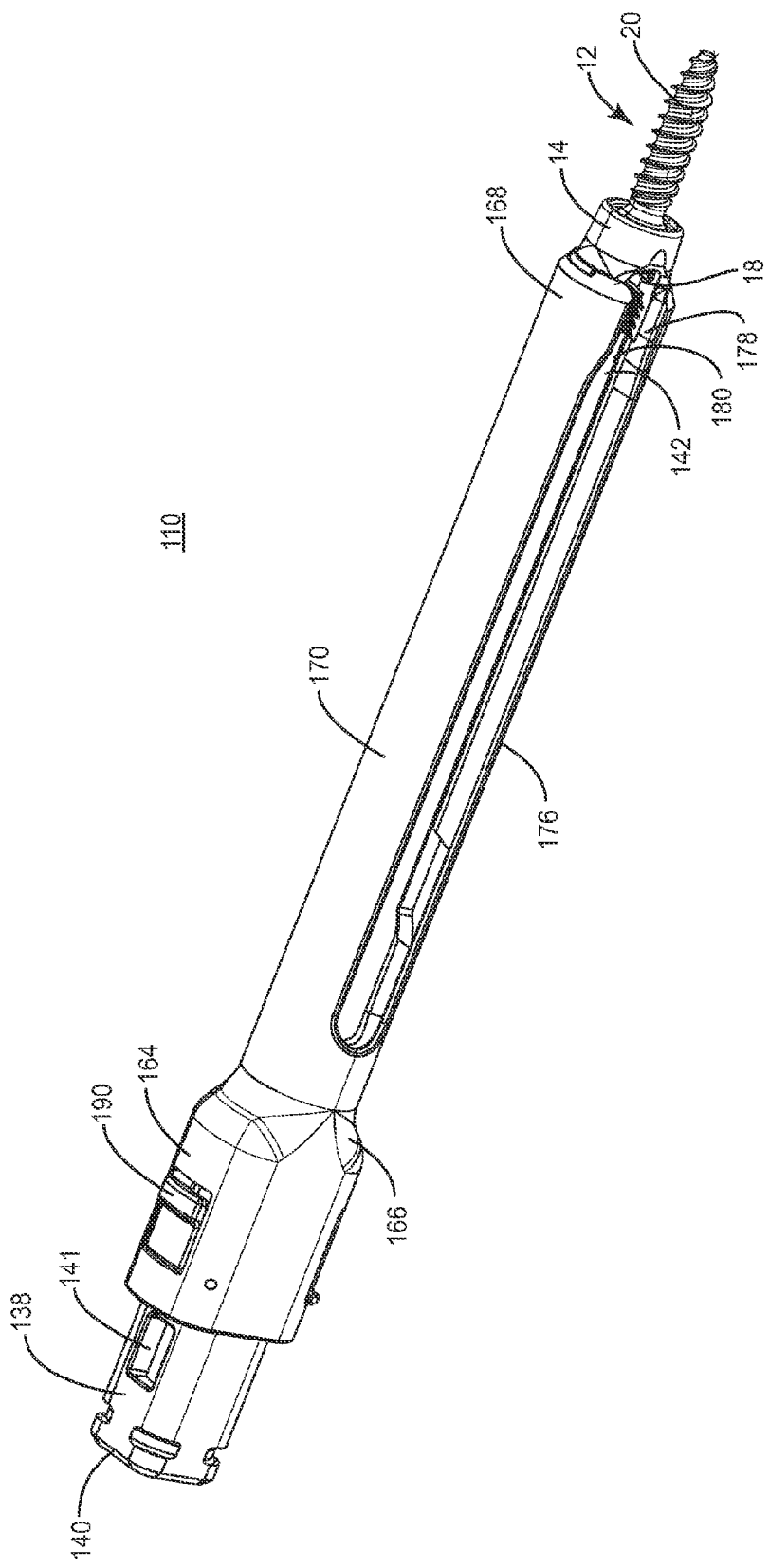
FIG. 10 is a perspective view of one embodiment of a system in accordance with the principles of the present disclosure.
Figure 14:
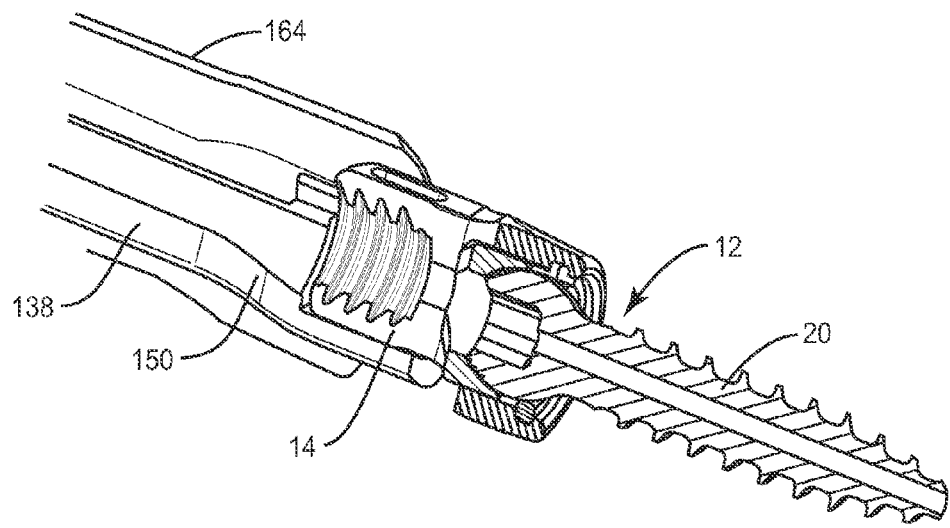
FIG. 14 is a break away cross section view of components of the system shown in FIG. 10.
Figure 15:
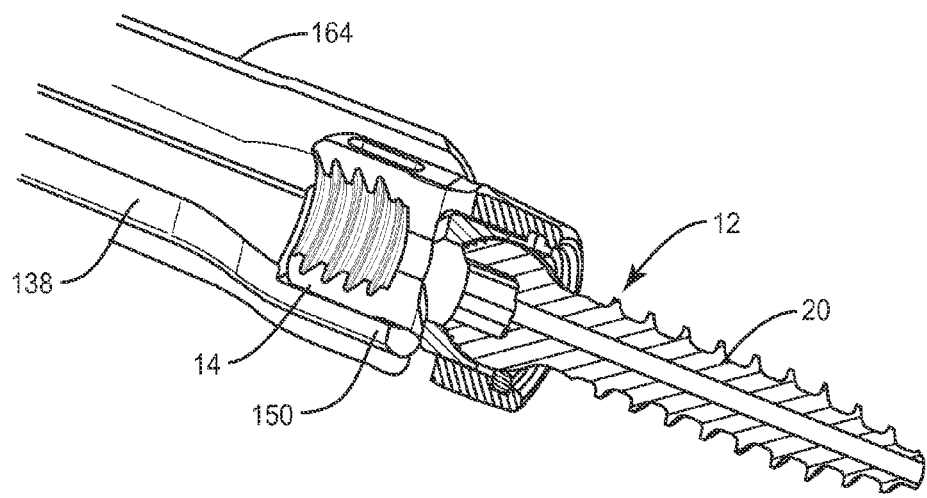
FIG. 15 is a break away cross section view of components of the system shown in FIG. 10.
Figure 16:
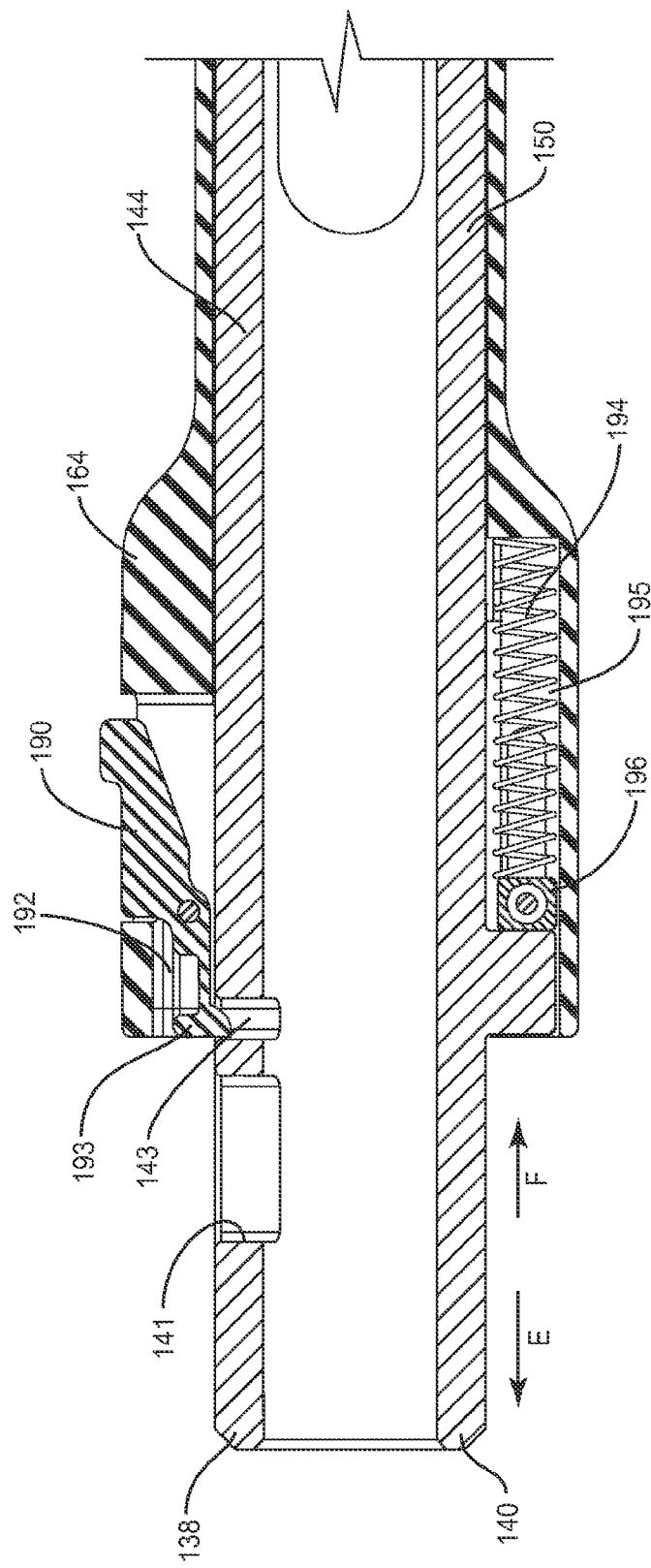
FIG. 16 is a break away cross section view of components of the system shown in FIG. 10.

Button 190 is engaged such that extender 138 is biased further in the second direction to position extender 138 and sleeve 164 in a locked position (FIG. 16) in the second orientation. In the second locked orientation, as shown in FIG. 10, distal end 142 of extender 138 is disposed within sleeve 164. Inner surfaces 172, 178 are facing and/or engaging in a close fitting contact with bone fastener 12 such that second end surfaces 26 are disposed in first and second cavities 174, 180 of sleeve 164. Extensions 170, 176 engage second side portion 36 such that planar faces 185, 187 engage second end surfaces 26 and arcuate faces 189, 191 engage outer surfaces 30. This configuration secures bone fastener 12 with extender 138/sleeve 164 and prevents ejection of bone fastener 12 from extender 138/sleeve 164 and/or rotation of receiver 14.

Upon fixation of bone fastener 12 and/or other components of spinal implant system 10, sleeve 164 and extender 138 are disposable in the first orientation to eject bone fastener 12 or extender 138. To eject and/or release bone fastener 12 from extender 138/sleeve 164, extender 138 is manipulated against the bias of spring 194 and further advanced in the first direction as shown by arrow F to the first orientation, as described above. Distal end 142 of extender 138 extends from distal end 168. The components of extender 138/sleeve 164 are manipulated to release bone fastener 12 from engagement such that projections 156, 158 are disengaged from slots 24 and bone fastener 12 is fixed securely with tissue according to the particular application.

In one embodiment, as shown in FIG. 17, spinal implant system 10, described above with regard to FIGS. 10-17, includes an extender 238, similar to extender 138, which includes a pair of resilient tabs 251 extending longitudinally along arms 244, 250 in a distal direction. Tabs 251 are resiliently biased inward to engage bone fastener 12 and pivotable relative to proximal end 240 of extender 238. Tab 251 engages locking cavities 32 of outer surfaces 30 disposed on opposing sides of bone fastener 12. Tabs 251 enhance fixation of extender 238 with bone fastener 12 and facilitate provisional capture of bone fastener 12 during advancement of sleeve 164. In one embodiment, tabs 251 are monolithically formed with extender 138.

It is envisioned that the spinal implant system may include one or a plurality of extenders, inserters, reducers, bone fasteners and/or vertebral constructs, which may be alternately sized and dimensioned, and arranged as a kit, according to the requirements of a particular application.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
    a first member comprising a proximal portion including a pair of spaced apart walls defining an implant cavity and a distal portion including a tissue penetrating portion, each of the walls including a first end surface defining a first locking cavity, a second end surface and an outer surface extending therebetween;
    a second member including a first arm having an inner surface that defines a first cavity and a second arm having an inner surface that defines a second cavity, the inner surface of the first arm including a first projection disposed within the first cavity and the inner surface of the second arm including a second projection disposed within the second cavity; and
    a third member including a first extension and a second extension that define a longitudinal cavity configured for disposal of the second member, the first and second extensions being spaced apart by a transverse passageway that extends through a bottommost end surface of the third member, the first extension having an inner surface that defines a first cavity and the second extension having an inner surface that defines a second cavity,
    wherein the third member is configured for axial translation relative to the second member between a first orientation such that the first and second projections of the second member extend distal to the third member to engage the first locking cavities and a second orientation such that the second end surfaces are disposed within the first and second cavities of the third member and the first end surfaces are engaging the inner surfaces of the first and second arms,
    wherein the inner surfaces of the first and second extensions are configured to directly and simultaneously engage the walls that define the implant cavity when the third member is in the second orientation, and
    wherein the system is configured to have a spinal rod positioned within the transverse passageway translate into the implant cavity without removing the rod from the system.

2. The spinal implant system of claim 1, wherein the second end surface defines a second locking cavity.

3. The spinal implant system of claim 1, wherein the first member includes a first side portion and a second side portion, the first side portion including the first end surfaces of each wall and the second side portion including the second end surfaces of each wall.

4. The spinal implant system of claim 1, wherein the inner surface that defines the first and second cavities of the third member each include a planar face engageable with the second end surface and an arcuate face engageable with the outer surface of a respective wall.

5. The spinal implant system of claim 1, wherein the inner surface that defines the first and second cavities of the second member each include a planar face engageable with the first end surface and an arcuate face engageable with the outer surface of a respective wall.

6. The spinal implant system of claim 1, wherein the first locking cavity comprises an elongated slot and the projection is elongated for mating engagement with the slot.

7. The spinal implant system of claim 1, further comprising an actuator having a linkage connected to the second member and the third member, the linkage including a handle configured to facilitate the axial translation.

8. The spinal implant system of claim 1, further comprising a linkage actuator having a first link connected to the second member and a second link connected to the third member, the first link including a handle configured to facilitate the axial translation.

9. The spinal implant system of claim 8, wherein the handle is rotatable relative to the second member.

10. The spinal implant system of claim 1, further comprising a linkage actuator having a first link connected to the second member at a first pivot point and a second link at a second pivot point, the second link being connected to the third member at a third pivot point, the first link including a handle extending from the second pivot point and being rotatable relative to the second member in a configuration to facilitate the axial translation.

11. The spinal implant system of claim 1, further comprising an actuator rotatable relative to the third member and engageable with the second member to facilitate and prevent the axial translation.

12. The spinal implant system of claim 1, wherein the inner surface of the first extension engages one of the walls that define the implant cavity and the inner surface of the second extension engages the other one of the walls that define the implant cavity.

13. The spinal implant system of claim 1, wherein the transverse passageway is unobstructed.

14. The spinal implant system of claim 1, wherein the first arm is fixed relative to the second arm.

15. The spinal implant system of claim 1, further comprising a linkage actuator having a first link connected directly to the second member and a second link directly connected to the first link and to the third member, the first link including a handle that is rotatable relative to the second member in a configuration to facilitate the axial translation.

16. The spinal implant system of claim 1, wherein a proximal end of the second member has a maximum diameter that is greater than that of the longitudinal cavity to prevent the proximal end of the second member from entering the longitudinal cavity.

17. The spinal implant system of claim 1, further comprising a rod reducer configured to translate the spinal rod from within the transverse passageway and into the implant cavity without removing the rod from the system.

18. A spinal implant system comprising:
a bone fastener comprising a receiver including a pair of spaced apart walls defining a U-shaped implant cavity and a shaft including a tissue penetrating portion, each of the walls including a first end surface defining a first locking slot, a second end surface defining a second locking slot and an outer surface extending therebetween and defining a third locking cavity, the bone fastener including a first side portion and a second side portion, the first side portion including the first end surfaces of each wall and the second side portion including the second end surfaces of each wall;
an extender including a proximal end and a distal end, and including a first cantilevered arm having an inner surface that defines a first capture cavity adjacent the distal end and a second cantilevered arm having an inner surface that defines a second capture cavity adjacent the distal end, the first and second cantilevered arms being spaced apart by a first passageway that extends through a bottommost surface of the extender, the inner surface adjacent the distal end including a first elongated projection that extends into the first cavity and a second elongated projection that extends into the second cavity, wherein the inner surface that defines the first and second cavities of the extender each include a planar face engageable with the first end surface and an arcuate face engageable with the outer surface of a respective wall such that the extender is engageable with the first side portion;
a sleeve extending between a proximal end and a distal end, and including a first cantilevered extension and a second cantilevered extension that define a longitudinal cavity configured for slidable disposal of the extender, the first and second cantilevered extensions being spaced apart by a second passageway that extends through a bottommost surface of the sleeve, the first extension having an inner surface that defines a first capture cavity and the second extension having an inner surface that defines a second capture cavity, wherein the inner surface that defines the first and second cavities of the sleeve each include a planar face engageable with the second end surface and an arcuate face engageable with the outer surface of a respective wall such that the sleeve is engageable with the second side portion; and
a linkage actuator having a first link connected to the proximal end of the extender at a first pivot point and a second link at a second pivot point, the second link being connected to the proximal end of the sleeve at a third pivot point, the first link including a handle extending from the second pivot point and being rotatable relative to the extender,
wherein the system is configured to have a spinal rod positioned within the first and second transverse passageways translate into the implant cavity without removing the rod from the system,
wherein the handle is engageable such that the sleeve is caused to axially translate relative to the extender in a first direction for disposal in a first orientation such that the first and second projections extend distal to the sleeve to engage the first locking slots and to axially translate relative to the extender in a second direction for disposal in a second orientation such that the second end surfaces are disposed within the first and second cavities of the sleeve and the first end surfaces are engaging the inner surfaces of the first and second arms with the projections disposed in the slots, and
wherein the inner surfaces of the first and second extensions are configured to directly and simultaneously engage the walls that define the implant cavity when the sleeve is in the second orientation.

19. A spinal implant system comprising:
a first member comprising a proximal portion including a pair of spaced apart walls defining an implant cavity and a distal portion including a tissue penetrating portion, each of the walls including a first end surface defining a first locking cavity, a second end surface and an outer surface extending therebetween;
a second member including a first arm having an inner surface that defines a first cavity and a second arm having an inner surface that defines a second cavity, the inner surface of the first arm including a first projection disposed within the first cavity and the inner surface of the second arm including a second projection disposed within the second cavity; and
a third member including a first extension and a second extension that define a longitudinal cavity configured for disposal of the second member, the first extension having an inner surface that defines a first cavity and the second extension having an inner surface that defines a second cavity,
wherein the third member is configured for axial translation relative to the second member between a first orientation such that the first and second projections of the second member extend distal to the third member to engage the first locking cavities and a second orientation such that the second end surfaces are disposed within the first and second cavities of the third member and the first end surfaces are engaging the inner surfaces of the first and second arms, and wherein the inner surfaces of the first and second extensions are configured to directly and simultaneously engage the walls that define the implant cavity when the third member is in the second orientation.

20. The spinal implant system of claim 19, wherein the first arm is fixed relative to the second arm.

\* \* \* \* \*